(12) United States Patent
Cawley

(10) Patent No.: US 6,240,766 B1
(45) Date of Patent: Jun. 5, 2001

(54) METHOD AND APPARATUS FOR ASSESSING THE RIPENESS OR FIRMNESS OF FRUIT AND VEGETABLES

(75) Inventor: Peter Cawley, London (GB)

(73) Assignee: Imperial College of Science, Technology and Medicine (GB)

( * ) Notice: Subject to any disclaimer, the term of this patent is extended or adjusted under 35 U.S.C. 154(b) by 0 days.

(21) Appl. No.: 09/380,861
(22) PCT Filed: Mar. 10, 1998
(86) PCT No.: PCT/GB98/00709
§ 371 Date: Nov. 11, 1999
§ 102(e) Date: Nov. 11, 1999
(87) PCT Pub. No.: WO98/40737
PCT Pub. Date: Sep. 17, 1998

(30) Foreign Application Priority Data

Mar. 10, 1997 (GB) .................................................. 9704908
Jul. 31, 1997 (GB) .................................................. 9716196

(51) Int. Cl.[7] .................................................. G01M 7/00
(52) U.S. Cl. .................................................. 73/12.01
(58) Field of Search .................. 73/11.01, 12.01, 73/12.04, 12.09, 12.12

(56) References Cited

U.S. PATENT DOCUMENTS

| 3,656,325 | * | 4/1972 | Peter | 68/3 SS |
| 4,055,842 | * | 10/1977 | Yakshin et al. | 341/132 |
| 4,131,012 | * | 12/1978 | Courtiol | 73/167 |
| 4,217,164 | | 8/1980 | La Mers . | |
| 4,542,639 | | 9/1985 | Cawley et al. . | |
| 5,315,879 | | 5/1994 | Crochon et al. . | |
| 5,811,680 | * | 9/1998 | Galili et al. | 73/579 |

FOREIGN PATENT DOCUMENTS

| 0 267 737 A2 | 5/1988 | (EP) . |
| 0 351 430 A1 | 1/1990 | (EP) . |
| 1-274059 | 11/1989 | (JP) . |
| WO 94/29715 | 12/1994 | (WO) . |

OTHER PUBLICATIONS

Patent Abstracts of Japan—vol. 010, No. 140 (P–458), May 23, 1986 & JP 60 260852 A (Toshiba), Dec. 24, 1985.

* cited by examiner

Primary Examiner—Max Noori
(74) Attorney, Agent, or Firm—Alston & Bird LLP

(57) ABSTRACT

Apparatus for testing fruit and vegetables to assess their ripeness includes an impactor device (28) comprising a bellows (30) which can be expanded and retracted by the application of pressurized air and vacuum via a support tube (32) for the bellows and which mounts an impactor (33) for tapping a fruit or vegetable item to be tested. The impactor has an internal slug movable relatively to the bellows (30) so that, when the bellows expands and stops upon its nose piece (36) contacting the surface of the item to be tested, the slug continues to move through the aperture (35) in the nose piece, under its own momentum, to tap the surface of the item. The slug incorporates a force transducer which, when the slug is tapped against the item, produces an electrical output signal in the form of a pulse corresponding to the reaction force and this pulse is processed to produce a signal indicative of the ripeness of the fruit.

24 Claims, 5 Drawing Sheets

METHOD AND APPARATUS FOR ASSESSING THE RIPENESS OR FIRMNESS OF FRUIT AND VEGETABLES

FIELD OF THE INVENTION

The present invention relates to a method and apparatus for testing fruit and vegetables to assess their firmness or ripeness.

BACKGROUND OF THE INVENTION

Knowing the degree of firmness or ripeness of fruit or vegetables (in the following description and claims referred to for convenience simply as fruit) is a factor of considerable commercial importance as it enables importers and distributors, for example, to assess the shelf-life of the fruit and meet the requirements of supermarkets and other retail outlets in this regard. When picked, even fruit from the same tree or plant is of different ripeness and any assessment made at this time is unreliable. Thus, boxes of fruit picked at the same time contain fruit with different degrees of ripeness. After picking, fruit is stored and transported under refrigerated conditions in order to prevent further ripening. Prior to supply to a retail outlet, the importer or distributor removes the fruit from cold store and exposes it to a warm environment to ripen it. It is at this stage that it is important to be able to assess or measure the ripeness of the fruit so that the importer or distributor may control the ripening to the degree necessary for the fruit to be supplied to the retail outlet with the required shelf-life.

One current method of testing fruit, such as avocado pears, to investigate the ripeness is to use a penetrometer. This is a hand-held instrument which comprises a pin or spike for pushing into the fruit, and a force meter which detects the force required to push the spike into the fruit and, hence, the degree of ripeness. Another instrument devised by the industry for testing the ripeness of an avocado pear is a firmometer. This instrument utilises a lever for applying a fixed force to the exterior of the fruit and measures the resulting deflection of the lever to provide a reading indicative of ripeness. U.S. Pat. No. 5,315,879 describes a measuring apparatus which may be used for measuring the firmness of fruit and other objects and which operates on similar principles to a firmometer. Both the penetrometer and firmometer type of instrument have the disadvantage that they damage or bruise the fruit being tested so that, particularly, in the case of the penetrometer, the fruit tested becomes unsaleable. Hence, they are used for testing on a selective basis and do not enable each individual fruit to be tested and individually assessed for shelf-life and treated and/or packaged accordingly.

EP-A-0 267 737 describes apparatus for testing all fruit in a batch so as to measure individual ripeness. It makes use of a transducer comprising a polymeric piezoelectric film having electrodes and secured by adhesive to a metal plate which in turn is mounted on a resilient block of foam material. The fruit to be tested is caused to impact on the transducer which produces an electrical output from the film. The metal plate is selected so as to have a mass which is small in relation to that of the fruit and is made of a metal which is non-resonant under the impact. The foam support is such that the film, the plate and the fruit move in contact during the impact. This arrangement has the result that the output signal from the film represents the resonance of the fruit due to the impact, which can be used as a measure of the firmness or ripeness of the fruit.

WO094/29715 describes a method and apparatus for testing the quality of a fruit by applying a dynamic force to the fruit and detecting the mechanical response of the fruit by means of piezoelectric film transducers supported on a displaceable supporting member. Hence, in so far as it measures the mechanical response of the fruit, it is similar to EP-A-0 267 727.

EP-A-0 351 430 and U.S. Pat. No. 4,542,639 both relate to the impact testing of engineering structures, such as laminates or honeycomb constructions, for delaminations and desponds. In the arrangement of EP-A-0 351 430, a sensor is mounted on a hammer which imparts a non-destructive impact to a material which is to be measured, and a signal produced by striking the material with the hammer is used to indicate the period of time of contact of the hammer with the material. The impact drive force applied to the hammer is removed by using a signal from the sensor as soon as the hammer comes into contact with the material being measured. U.S. Pat. No. 4,542,639 describes the impact testing of structures in which a structure is struck by an impactor associated with a force transducer the output of which is related to the force which the transducer experiences on impact and encompasses a frequency range including the lowest frequencies which that force contains to any substantial degree. The impactor may be driven by an electromagnetic arrangement. The maximum amplitude indicates whether the structure is faulty or not.

U.S. Pat. No. 4,217,614 describes apparatus for automatically applying pressure sensitive labels to objects which utilises an application device in the form of a bellows which is pressure/vacuum operated in order to extend and contract the bellows in a label applying operation.

SUMMARY OF THE INVENTION

It is an object of the present invention to provide a method of and apparatus for testing a fruit to assess or measure its ripeness and to provide such a method and apparatus which are able to produce more consistent and reliable measurements of ripeness than hitherto known instruments and which produce such measurements without unacceptable damage to the fruit being tested.

From one aspect, the present invention consists in a method of testing a fruits to assess its ripeness, comprising the steps of applying a driving force to an impactor so as to cause the impactor to strike the fruit, detecting the reaction by means of a force transducer incorporated in the impactor and producing an electrical output signal representing a reaction force generated by the impactor striking fruit, and processing the output signal to produce a measurement indicative of the ripeness of the fruit, characterised by terminating the application of the driving force before the impactor strikes the fruit so that the impactor strikes the fruit with an impact in the form of a tap and the transducer produces an electrical output signal in the form of a pulse in response to the reaction force generated by the impactor striking the fruit.

From another aspect, the invention consists in apparatus for testing a fruit to assess its ripeness, comprising at least one impactor having a force transducer which, when the impactor strikes the fruit, produces an electrical output signal representing the reaction force generated by the impact, driving means operable to apply a driving force to the impactor and urge the impactor towards the fruit, and means for processing the output signal to produce a signal indicative of the ripeness of the fruit, characterised in that the driving means is operated so as to terminate the application of the driving force before the impactor strikes the fruit, whereby the impactor strikes the fruit with an impact in the form of a tap and the transducer produces an output signal in the form of a pulse, said output signal being linearly related to the reaction force to which the transducer is subjected by reason of the impact.

The force of the tap with which the fruit is struck must be of such a magnitude that it is not so small that the skin of the fruit absorbs most of the blow and not so hard as to damage the fruit.

According to one preferred embodiment of the invention, the impactor is provided in a plunger means which is adapted to move the impactor towards and away from a fruit item. Preferably, the plunger means is a bellows which can be expanded by the admission thereto of pressurised air and retracted by application of a vacuum. In this embodiment, the impactor is movable relatively to the plunger means so that, when the plunger means stops moving towards a fruit item whose condition is to be assessed, the impactor will continue to move under its own momentum to strike the surface of the fruit. By adjusting the speed of the plunger means and the distance that the impactor travels, the force with which the impactor strikes the surface of the fruit is of the desired magnitude, as explained above.

When a fruit, such as an avocado pear, is tapped with the impactor, the reaction force resulting from the tap is detected by the force transducer and the latter produces an electrical output signal in the form of a single pulse corresponding to the reaction force. Both the peak value and the duration of this pulse depend on the firmness and, therefore, the ripeness of the fruit. The peak value of the reaction force and resulting electrical pulse increase as the firmness of the fruit increases whilst the duration of the pulse decreases with increase in firmness. The electrical pulse can be processed in several different ways in order to derive from the pulse an indication of the ripeness of the fruit tapped. Hence, the measurement of ripeness may be based on peak force or the peak value of the resulting electrical output pulse. In order for such a measurement to be reliable, the momentum of the impactor at the instant before striking the fruit must be constant for the fruits being tapped. In practice, this may be difficult to achieve with irregularly shaped fruit. Alternatively, the output signal may be processed on the basis of duration in order to produce an indication of ripeness. The duration is only a weak function of the momentum of the impactor on striking the fruit so that maintaining constant momentum at this stage is not as important as when processing is based on peak value. However, problems may occur with the accuracy of measurement based on duration because of the difficulty in accurately defining the duration of a pulse owing to the fact that there is frequently a "tail" on the pulse.

Instead of time domain measurements, as described above, the signal processing may involve some form of frequency domain processing. In one form of the latter, the output signal is electronically resolved into a frequency spectrum encompassing a predetermined frequency range, including the lowest frequency which the output pulse comprises to any significant degree, and the frequency components in the frequency spectrum are processed as a function of the reaction force. Preferably, such a processing stage comprises computing a graph of the variation of the frequency components in the frequency spectrum as a function of the reaction force based on a logarithmic scale (frequency along the x-axis, log force along the y-axis) and measuring the ripeness based on the area of a predetermined zone below the graph and between, for example, two lines of constant force F1,F2 corresponding respectively to the log values of the maximum force component and a force component 25 dB less than the maximum. In order to provide a numerical output directly related to the ripeness of each individual fruit of a particular species, the measured area of the graph may be presented as a percentage of a fixed reference area which, in the present example, may be selected as the rectangular area defined between the lines of constant force F1, F2, and the same frequency limits as the measured area. The lower end of the frequency range may be substantially zero frequency and the upper end may be in the range from 2–5 kHz. The area calculated is substantially independent of the level of the spectrum at zero frequency and is therefore only a very weak function of the momentum of the impactor at impact.

Another form of frequency domain processing is electronically to plot a graph of force against frequency on a linear force scale and simply integrate force with respect to frequency, thus obtaining the area under the curve. This avoids the need to define predetermined down points as is required by the previously described frequency domain process. The area under the curve of the graph increases as the firmness increases. However, with this method of processing, the momentum of the impactor must be controlled very accurately as the area under the curve is proportional to momentum and, in practice, this method may not be a very attractive.

One way of alleviating the effect of the momentum of the impactor at impact on the momentum dependent measurements described above is to compute the momentum H and normalise the result to produce a new measurement parameter given by peak force/H. Momentum H is given by the expression:

$$H = \int P(t)dt$$

where P(t) is the force as a function of time. This parameter works to provide acceptable results but the peak force may not always be well defined. An alternative, which uses all the points in the electrical output pulse representing the force-time function, is to compute the integral of the square of the pulse S, which is given by the expression;

$$S = \int [P(t)]^2 dt$$

Thus, normalising the above expression, the resulting parameter S/H gives a more reliable measure of the firmness of the fruit.

The area under the force-frequency curve of the frequency domain processing described above may also be normalised by dividing by momentum H although, in this case, a simpler normalisation is to divide by X(0) which is the dc (zero frequency) level of the spectrum which is obtained via the Fourier analysis utilised for converting from force-time to force-frequency.

The preferred method of signal processing is to use either the peak force/H or the S/H parameter, as described above. This has the advantage of not requiring a Fourier transform and is quicker to implement than frequency domain techniques. It can also be implemented in analogue electronics, rather than digital electronics, which makes the signal processing system potentially cheaper.

In order that the measurement can be provided as a numerical output directly indicative of the ripeness of the fruit, it will be necessary to calibrate the measurements produced against known ripening data for each species of fruit and its individual cultivars.

The invention enables a ripeness test to be performed in any position on a fruit and the tap may be applied to the fruit either manually or mechanically. In an automated system having a mechanically operated impactor for tapping each individual fruit, in turn, to investigate the individual ripeness of the fruit, the resulting signals indicative of the ripeness may be used, for example, to control a gating mechanism which directs the fruit to different collecting stations depending on the degree of ripeness, and hence shelf-life, indicated by the ripeness signal.

BRIEF DESCRIPTION OF THE DRAWINGS

In order that the present invention may be more readily understood, reference will now be made to the accompanying drawings, in which.

DETAILED DESCRIPTION OF THE PREFERRED EMBODIMENT

Figure 1:
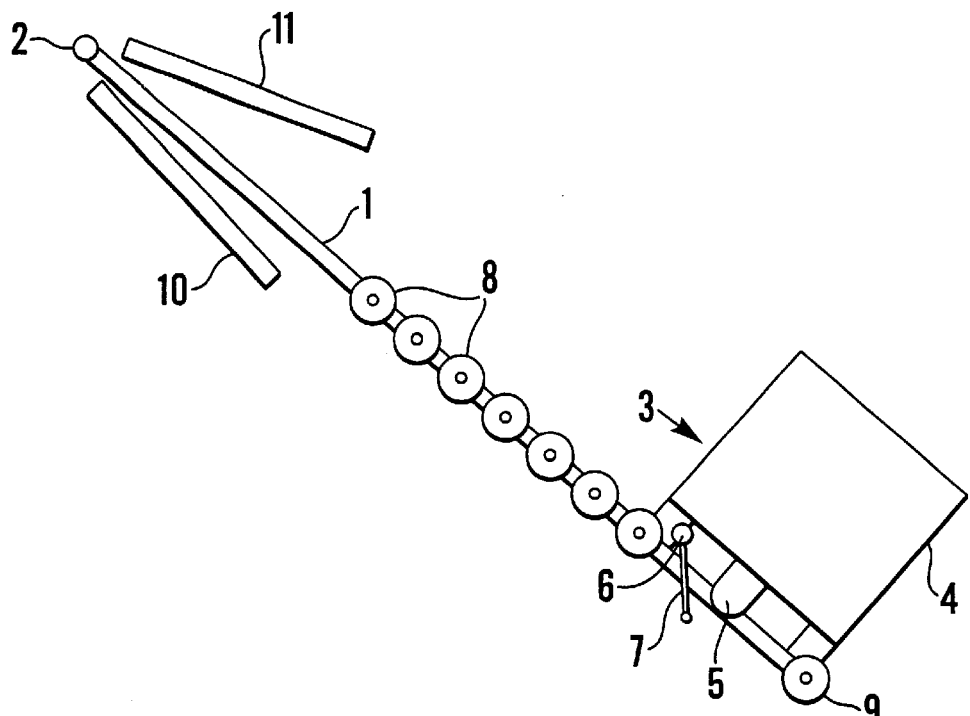
FIG. 1 is a schematic side view of one embodiment of the invention.

The apparatus illustrated in FIG. 1 is designed to tap test fruit, such as avocado pears, as they are conveyed along a so-called "singulator" which is used in sorting depots to place fruit into individual cups from which they are deposited into different hoppers depending on the degree of ripeness sensed by the test. The apparatus includes an impactor arm 1 which is pivoted at one end 2 above the singulator or conveyor (not shown) arranged to convey the items of fruit one at a time beneath the arm. At its outer end, the arm mounts the impactor device 3. The latter comprises a solenoid 4 having its armature 5 projecting at one end from the solenoid casing and serving as an impactor which is arranged to tap the fruit passing beneath the arm. The armature 5 is advanced to apply a tap to a fruit in response to an electrical driving pulse applied to the solenoid and is spring biassed to return to its retracted position. The armature incorporates a force transducer in the form of a piezoelectric crystal which produces an electrical output pulse in response to the reaction force exerted on the armature as a result of applying a tap to a fruit. The solenoid 4 is triggered to apply a tap in response to the actuation of a microswitch 6 by a fruit travelling beneath the impactor and engaging a downwardly projecting actuating arm 7 of the microswitch.

Between the solenoid 4 and the pivot 2, the arm 1 is fitted with rollers 8 to permit the arm to ride smoothly over fruit travelling beneath and engaging the arm preparatory to being tapped by the impactor. The fruit is protected from damage by the outer end of the arm by a further roller 9. Suitable stops 10, 11 are mounted below and above the arm adjacent its pivot in order to limit movement of the arm and prevent it from dropping too low and engaging the conveyor or being raised too high.

Figure 2:
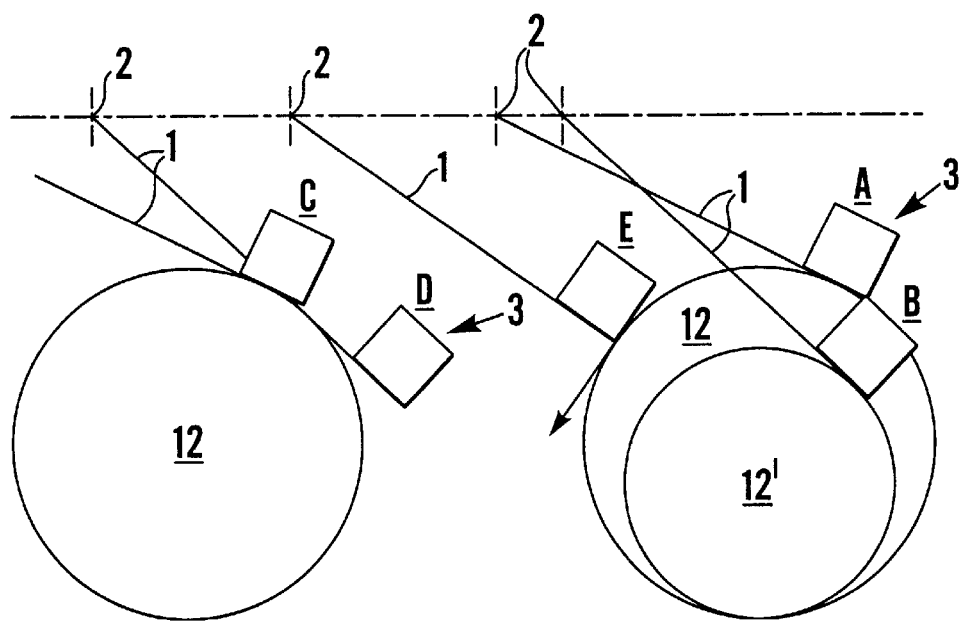
FIG. 2 is a schematic side view illustrating the motion sequence of the impactor device of FIG. 1 as it is engaged by fruit moving along a conveyor beneath the impactor device (for clarity the pivot position of the device is moved horizontally in this Figure whereas, in reality the pivot of the device is fixed and the fruit travels past the device)

The conveyor is of a known construction and, desirably, it should position the avocado pears or other fruit, under the impactor with the widest or most bulbous part of the fruit below the impactor. The fruit may be advanced along the conveyor with a rolling motion or be stationary about its axis. Referring also to FIG. 2, as each fruit 12 travels below the impactor arm 1, it engages the arm and pushes it upwards so as to move the impactor 3 into a position for tapping the fruit. When the fruit and impactor are in a predetermined position relative to one another, the fruit actuates the microswitch 6 by engaging the actuating arm 7 so that an electrical diving pulse is supplied to fire the solenoid 4 and the armature 5 is actuated to tap the fruit.

The firing position of the solenoid is at A on large fruit 12 and at B on small fruit 12' whilst the first contact position is C on large fruit and D on small fruit. These differences in contact positions are accommodated by firing the solenoid with the microswitch 6. After tapping, each fruit continues to travel beneath the arm 1 and subsequently the arm is released from the fruit (position E) and returns to a rest position against the lower stop preparatory to engaging the next fruit on the conveyor line. The roller 9 at the outer end of the arm protects the fruit from damage as the arm is released.

Figure 3:
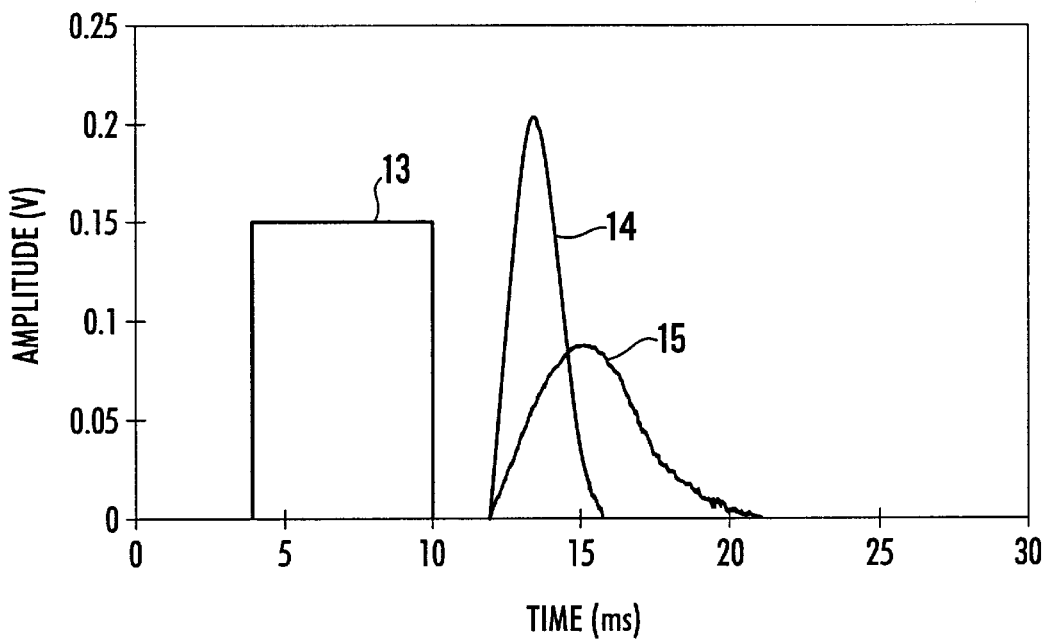
FIG. 3 is a voltage/time graph illustrating the shapes of the electrical driving pulse for the impactor and the output pulses resulting from tapping fruits of different firmness.

As shown in the graph of FIG. 3, the solenoid driving pulse 13 is a square pulse and has finished before the tap impacts on a fruit so that the solenoid 4 does not drive the armature into the fruit. The reaction force resulting from a tap applied by the solenoid armature striking the fruit is detected by the force transducer and is reproduced as a single electrical output pulse similar to pulses 14, 15 shown in FIG. 3. The peak value and duration of the resulting output pulse depends on the firmness and therefore the ripeness of the fruit. Hence, the pulse 14 represents the pulse resulting from a tap test on an unripe or hard avocado whilst pulse 15 results from a tap test on a ripe or soft avocado. These output pulses may be processed in any of the ways described above in order to produce a measurement indicative of the ripeness of the fruit.

Figure 4:
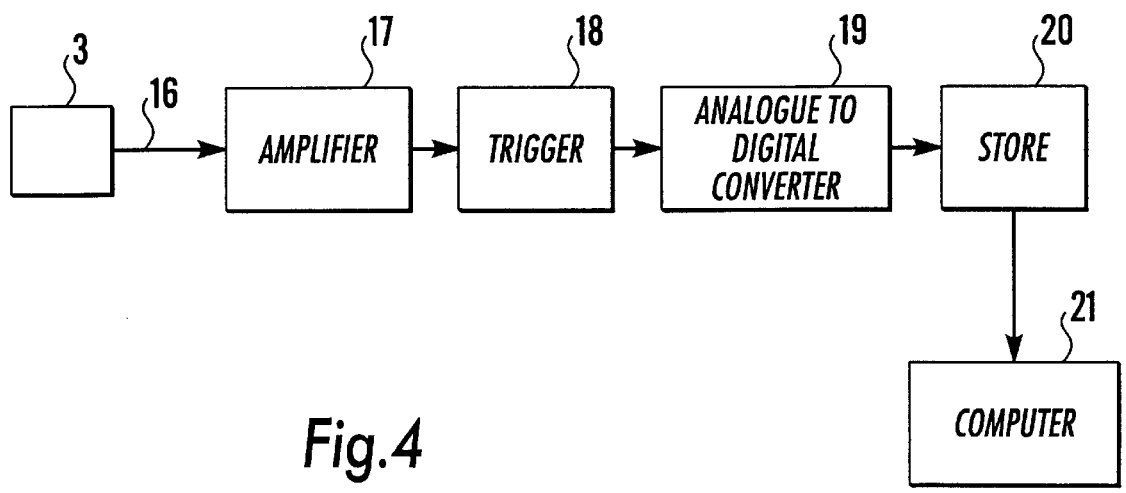
FIG. 4 is a block circuit diagram of signal processing circuitry suitable for use with the invention.

FIG. 4 illustrates an electronic circuit for use with the tapping device described above and for processing the electrical output pulses produced by the device upon tapping fruit. The output pulses from the piezoelectric transducer of the impactor device 3 are fed by way of leads 16, an amplifier 17 and trigger unit 18 to an analogue-to-digital converter 19 and then to a buffer store 20. The trigger unit 18 operates in response to actuation of the microswitch 6 and ensures that the value of the output from the amplifier 17 covers the full duration of the pulse. When required, the output from the store 20 is fed to a computer 21 which processes the digital signal from the store in any of the ways described above to produce a measurement indicative of the ripeness of the fruit. In order that the measurement can be provided as a numerical output directly indicative of the ripeness, it will be necessary to calibrate the measurements produced against known ripening data for each species of fruit and its individual cultivars.

Figure 5:
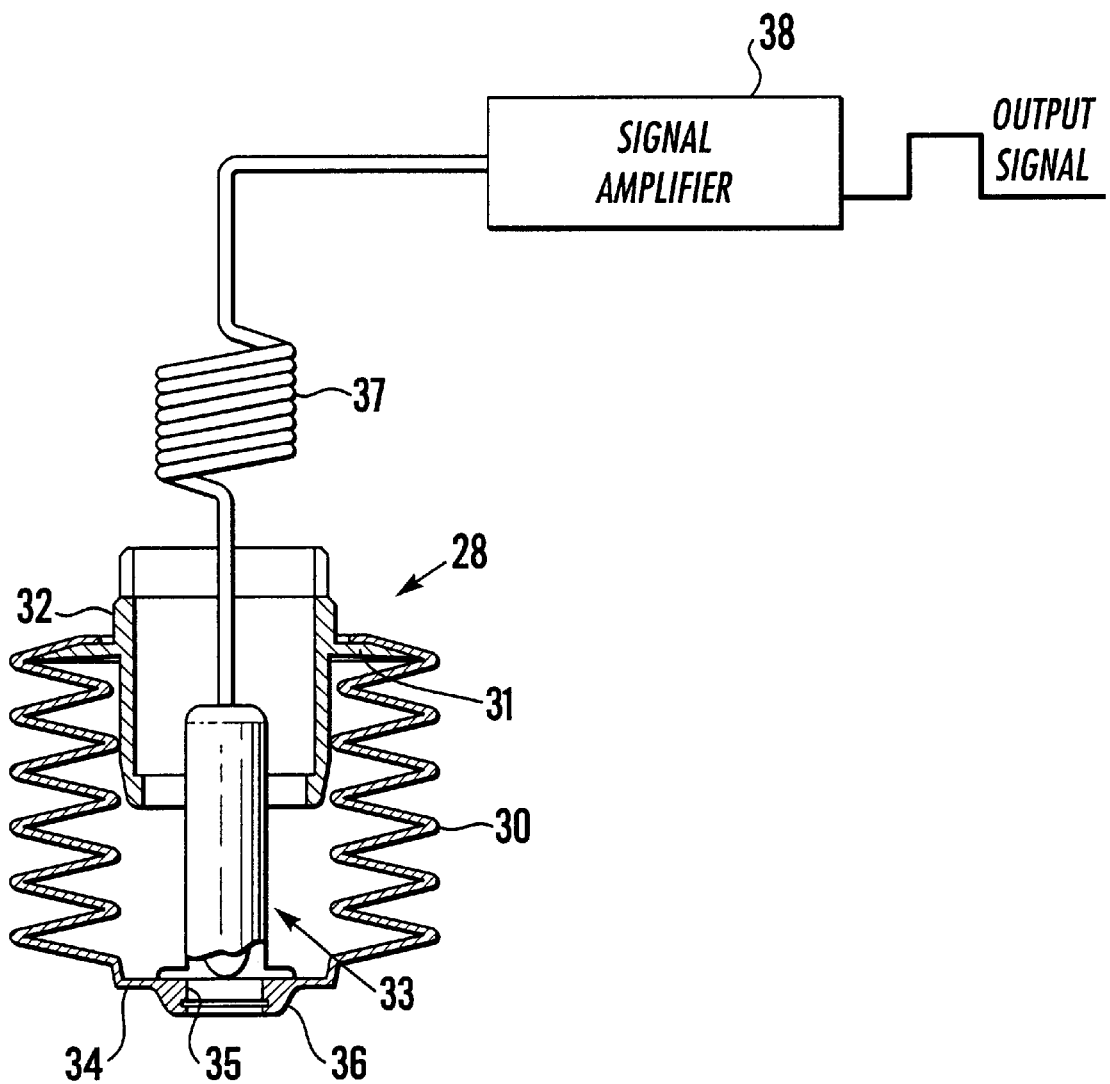
FIG. 5 is a diagrammatic, part sectional elevation, of another embodiment of the invention.
Figures 6, 6A:
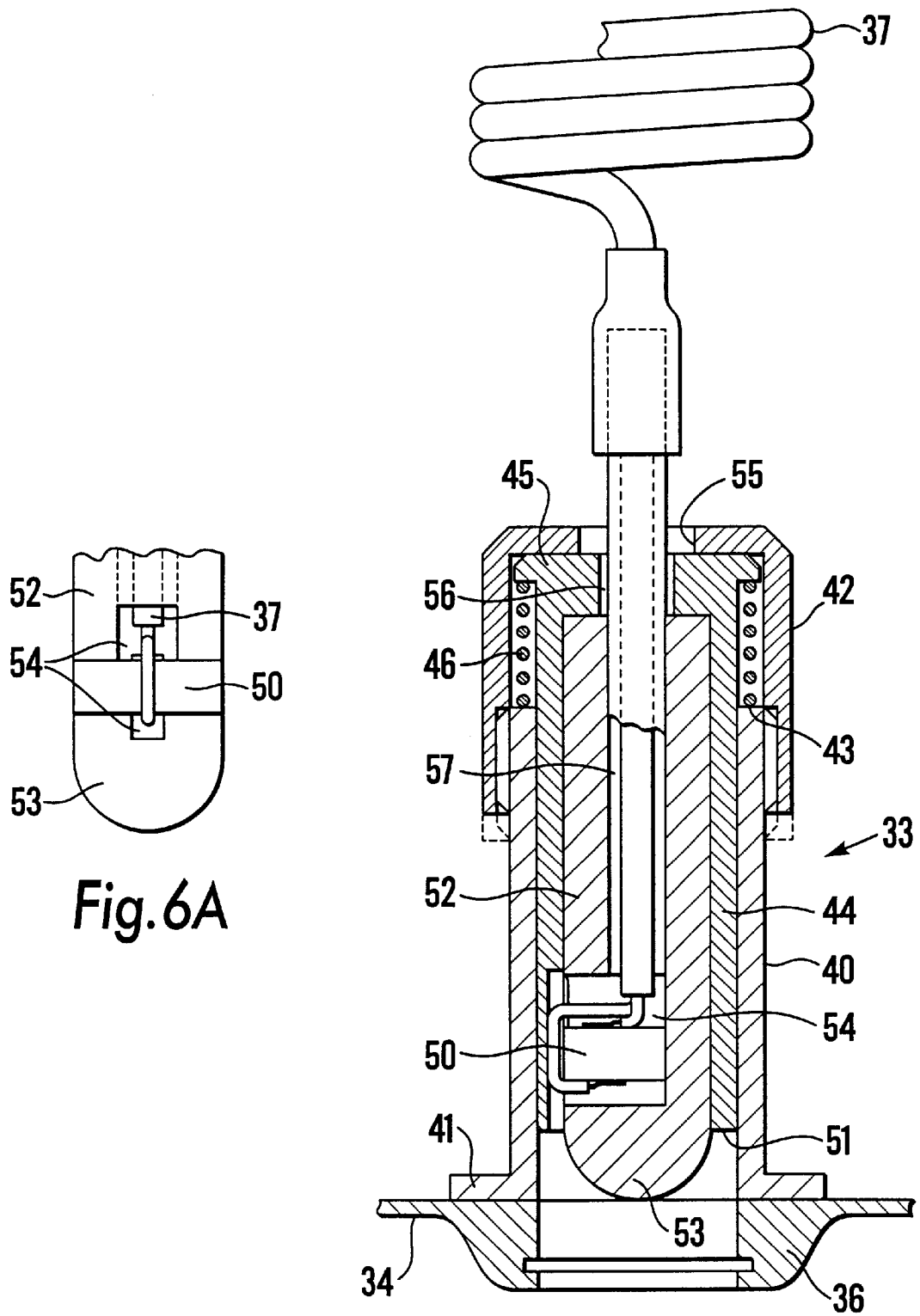
FIG. 6 is a section on an enlarged scale of the impactor of the embodiment of FIG. 5.
FIG. 6A is a fragmentary view of the impactor of FIG. 6.

Referring now to FIGS. 5 and 6, an alternative embodiment of the impactor device 28 comprises a bellows 30 of resilient material, such as, plastics or synthetic rubber, and of lightweight construction. Such a bellows is already known in connection with labelling machines for example as described in U.S. Pat. No. 4,217,164. The bellows is mounted on the projecting annular flange 31 of a rigid, tubular support 32. Means (not shown) are provided for applying a vacuum to the bellows to hold it in a retracted disposition, as illustrated in FIG. 5, and when appropriate, to supply pressurised air to the bellows to expand it downwardly (as viewed in FIG. 5).

An impactor 33 is mounted on the inner surface of the free end 34 of the bellows above an aperture 35 in a shaped nose piece 36 at the free end 34. The impactor 33 is movable with the bellows when the bellows is expanded and retracted. It is electrically coupled by wires 37 to an amplifier 38 for signals from the impactor.

The impactor 33 is shown in more detail in FIG. 6. It is mounted in a tubular housing 40 having an out-turned flange 41 at one end mounting the impactor on the inner surface of the free end 34 of the bellows 30. A cap 42 is provided at the opposite end of the housing which with said opposite end defines an Internal annular shoulder or abutment 43.

The impactor, itself, comprises an inner housing 44 slidably disposed in housing 40. The end of the inner housing 44 adjacent the cap 42 is provided with a flange 45. A compression spring 46 is positioned around the inner housing and bears at one end on the shoulder 43 and at its opposite end on the flange 45 so that the inner housing is urged upwardly (as viewed in FIG. 6). The upward movement of the inner housing is limited by engagement of the inner housing against the cap 42.

Secured within the inner housing 44 is a solid slug 52 which mounts a piezoelectric transducer 50 adjacent the end 51 of the inner housing remote from the cap 42. The end 53 of the slug projects from the end 51 of the inner housing for striking a fruit to be tested and as part spherically shaped. The transducer 50 is mounted in contact with the slug and the signal wires 37 are fed to a cavity 54 providing access to opposite sides of the transducer and permitting connection of the wires 37 thereto, via an aperture 55 in the cap and passageways 56,57 in the inner housing and slug (see also FIG. 6A).

In operation fruit or vegetable items are conveyed in sequence by a conveyor past the bellows. When a fruit item is underneath the bellows, expansion of the bellows is effected in response to control means which can be similar to the control means used for labelling, as described in the aforementioned U.S. Pat. No. 4,217,164. The bellows expand until the nose piece 36 at the free end contacts the fruit or vegetable item. At that instant further expansion of the bellows stops. However, the impactor 33 which moves with the expanding bellows continues moving until the slug 52 impacts against the surface of the fruit or vegetable item. The reaction force exerted on the slug 52 causes the piezoelectric transducer 50 in contact with the slug to produce a signal which can then be processed in the same way as described in connection with FIG. 4.

Figure 7:
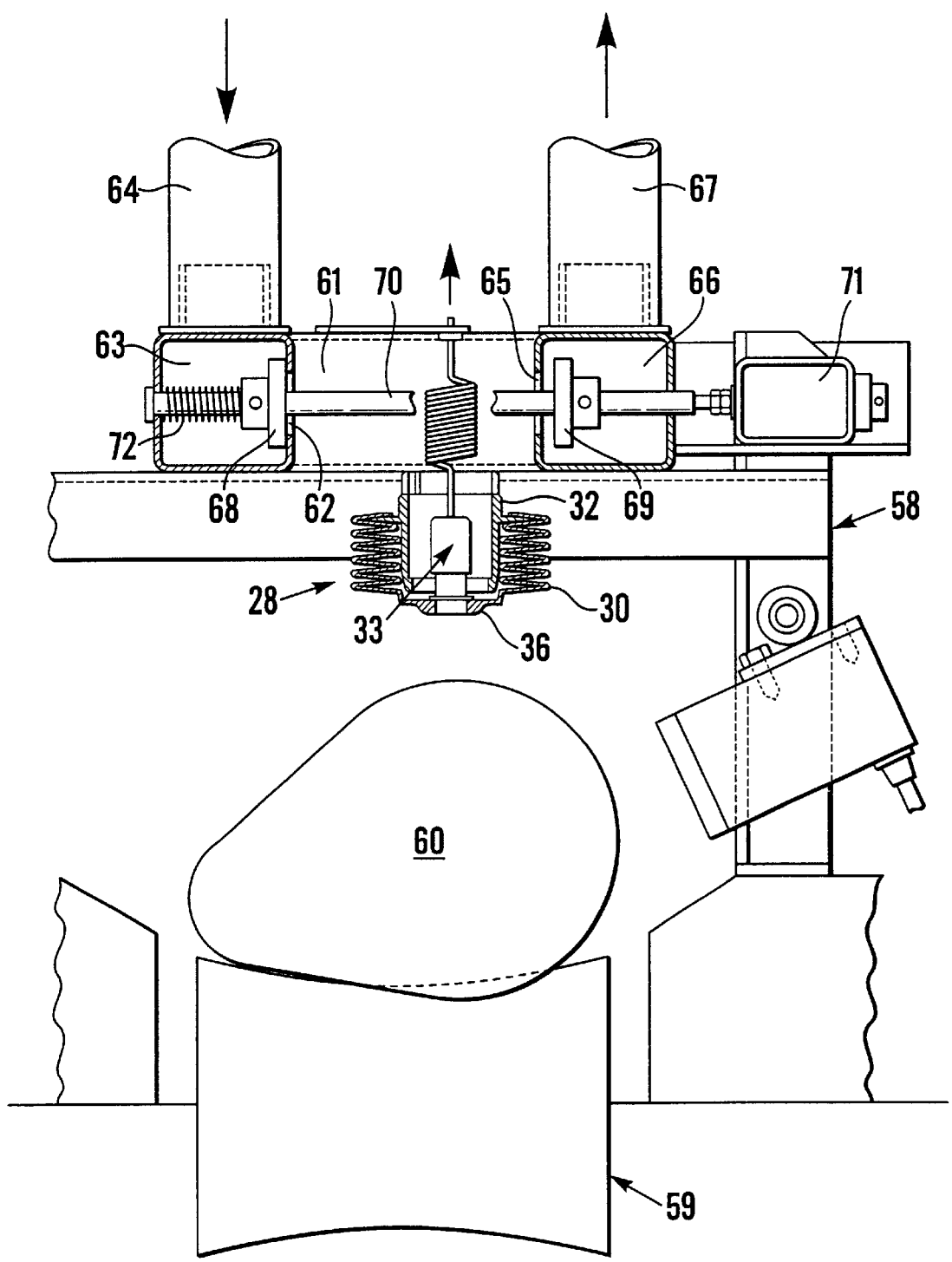
FIG. 7 is a view, partly in section, of apparatus embodying the impactor device of FIGS. 5 and 6 and taken transverse to the fruit conveyor.

In FIG. 7, the impactor device 28 is shown installed in a ripeness testing machine and mounted above a fruit 60 which is passing below the device. The latter is mounted on a frame structure 58 which is disposed above a conveyor 59 upon which the fruit 60 is transported.

The tubular support 32 for the bellows of the impactor device communicates with a chamber 61 mounted on the frame structure 58 above the device. The chamber 61 is connected at one side, via a port 62, to a pressurised air chamber 63 which is coupled to a source of air pressure by an inlet conduit 64. At its opposite side, the chamber 61 is connected, via a port 65, to a vacuum chamber 66 which is connected to a source of vacuum by an outlet conduit 67. The ports 62,65 are controlled by valve members 68,69 attached to a slidable valve rod 70 which is reciprocated by means of an electrical solenoid 71 and a return spring 72. The spring 72 urges the valve members 68,69 into positions in which the air inlet port 62 is closed and the vacuum port 65 is open so that vacuum is applied to the support tube 32 and the bellows 30 are retained in a retracted rest position. Actuation of the solenoid 71 slides the valve control rod 70 against the action of the spring 72 to open the air inlet port 62 and close the vacuum port 65, thereby momentarily expanding the bellows so as to cause the nose 36 to contact a fruit 60 conveyed below the impactor device and the impactor to tap the fruit and produce an output pulse from the transducer 50. The solenoid 71 can be controlled in any convenient manner so as to actuate the impactor device as each fruit 60 is advanced below it. The solenoid is triggered so as to open the valve member 68 only briefly and apply air pressure to the bellows for a sufficient time to produce a driving force to initiate movement of the bellows and impactor towards the fruit, the arrangement being such that the impactor striking the fruit under its own momentum when the nose piece 36 of the bellows contacts and stops against the fruit. Immediately, thereafter, the bellows are contracted by exhaustion of air therefrom through the vacuum port 65 and vacuum outlet conduit 67 to return the impactor device to its rest position.

In order to optimise the ripeness measurement for each fruit, two or more impactor devices 28 may be mounted side-by-side in a row transversely of the conveyor 59 for simultaneously tapping each fruit so as to produce an output signal for each of a plurality of positions along the fruit axis disposed transversely to the direction of movement of the conveyor. The conveyor 59 may be adapted to rotate each fruit as it is advanced by the conveyor and a plurality of the impactor devices 28 may also be mounted in succession, or in successive rows, along the conveyor for successively tapping each fruit and producing an output signal for each of a plurality of positions about the fruit.

Whilst particular embodiments have been described, it will be understood that modifications can be made without departing from the scope of the invention as defined by the appended claims. For example, the signal processing may not require that the analogue output signal from the piezoelectric transducer be converted into a digital signal for processing by the computer, in which event, the analogue to digital converter 19 may be omitted from the circuit. Moreover, the rollers 8,9 on the impactor arm 1 many be replaced by strips of low friction material, such as PTFE.

What is claimed is:

1. A method of testing a fruit to assess its ripeness, said method comprising the steps of:

providing an impactor for striking said fruit, said impactor incorporating a force transducer for detecting a reaction force generated by said impactor striking said fruit and producing an electrical output signal representing said reaction force;

applying a driving force to said impactor so as to cause said impactor to strike said fruit;

terminating application of said driving force before said impactor strikes said fruit so that said impactor strikes said fruit with an impact in the form of a tap, said transducer thereby producing an electrical output signal in the form of a pulse in response to said reaction force generated by said impactor striking said fruit, and processing said output signal to produce a measurement indicative of the ripeness of said fruit.

2. A method according to claim 1, wherein the processing of the output signal involves determining the peak value of the reaction force.

3. A method according to claim 1, wherein the processing of the output signal involves resolving the output signal into a frequency spectrum encompassing a predetermined frequency range and processing the frequency components of the spectrum as a function of the reaction force.

4. A method according to claim 3, including computing a graph of the variation of the frequency components in the frequency spectrum as a function of the reaction force based on a logarithmic scale and producing the measurement of ripeness based on the area of a predetermined zone below the graph.

5. A method according to claim 3, wherein the processing of the output signal involves integrating force with respect to frequency for a plot of force against frequency on a linear force scale.

6. A method according to claims 1, wherein the processing of the output signal involves computing the parameter S which is given by the equation $$S = \int [P(t)]^2 dt$$

where P(t) is the reaction force as a function of time.

7. A method according to claim 1, wherein the effect of the momentum of the impactor, at impact, on the ripeness measurement is alleviated by normalising the measurement.

8. A method according to claim 7, wherein the normalisation involves dividing the measurement by the momentum H of the impactor at impact which is given by the expression $$H = \int P(t) dt$$

where P(t) is the reaction force as a function of time.

9. A method according to claim 4, wherein the frequency spectrum has a DC level and the value obtained for said area below said graph is normalised by dividing by the DC level of the spectrum.

10. A method according to claim 1, wherein the fruit is rotated and is struck by a plurality of the impactors so that output pulses are produced for a plurality of positions about the fruit.

11. Apparatus for testing a fruit to assess its ripeness, said apparatus comprising:

at least one impactor, said impactor having a force transducer which, when said impactor strikes said fruit produces an electrical output signal representing a reaction force generated by said impactor striking said fruit;

driving means for applying a driving force to said impactor to urge said impactor towards said fruit, said driving means being operable so as to terminate application of said driving force before said impactor strikes said fruit, whereby said impactor strikes said fruit with an impact in the form of a tap and said transducer produces an output signal in the form of a pulse, said output signal being linearly related to said reaction force to which said transducer is subjected by reason of said impact; and means for processing said output signal to produce a signal indicative of the ripeness of said fruit.

12. Apparatus according to claim 11, wherein the impactor is mounted in a plunger means which is adapted to move the impactor towards and away from the fruit.

13. Apparatus according to claim 12, wherein the plunger means is a bellows which is arranged to be expanded by the admission of a pressurised gas and retracted by the application of vacuum.

14. Apparatus according to claim 12, wherein the impactor is movably mounted relatively to the plunger such that, when the plunger stops moving towards the fruit, the impactor continues to move under its own momentum so as to strike the fruit.

15. Apparatus according to claim 11, wherein the impactor comprises the armature (4) of an electrical solenoid (4) serving as the driving means.

16. Apparatus according to claim 11, wherein the impactor (1) is mounted at the end of a pivoted arm (1) which is engageable by the fruit advanced beneath the arm to position the impactor for striking the fruit.

17. Apparatus according to claim 16, wherein the arm mounts a plurality of rollers, PTFE strips or other friction reducing means in positions to engage the fruit advanced beneath the arm to permit the arm to ride smoothly over the fruit.

18. Apparatus according to claim 11, wherein the transducer comprises a piezoelectric crystal.

19. Apparatus according to claim 11, including conveying means for advancing the fruit relatively to the impactor.

20. Apparatus according to claim 19, wherein the impactor is triggered by the fruit contacting a microswitch as it is advanced by the conveying means relatively to the impactors.

21. Apparatus according to claim 19, including at least two of the impactors mounted side-by-side transversely to the conveying means so as to tap the fruit and produce an output signal for each of a plurality of positions along an axis of the fruit which axis is disposed transverse to the direction of movement of the conveying means.

22. Apparatus according to claim 19, wherein the conveying means is adapted to rotate the fruit as it is advanced by the conveying means, and a plurality of the impactors are mounted in succession along the conveying means so as to tap the fruit and produce an output signal for each of a plurality of positions about the fruit.

23. Apparatus for testing a fruit to assess its ripeness, said apparatus comprising:

at least one impactor, said impactor having a force transducer which, when said impactor strikes said fruit produces an electrical output signal representing a reaction force generated by said impactor striking said fruit;

a bellows mounting said impactor;

control means for alternately admitting a pressurised gas and applying a vacuum to said bellows, whereby to expand said bellows and apply a driving force to said impactor for urging said impactor towards said fruit, and thereafter retract said bellows;

said control means being arranged to terminate said application of pressurised gas before said impactor strikes said fruit, whereby said impactor strikes said fruit with an impact in the form of a tap and said transducer produces an output signal in the form of a pulse, said output signal being linearly related to said reaction force to which said transducer is subjected by reason of said impact; and means for processing said output signal to produce a signal indicative of the ripeness of said fruit.

24. Apparatus for testing a fruit to assess its ripeness, said apparatus comprising:

a plurality of impactors, each said impactor having a force transducer which, when said impactor strikes said fruit, produces an electrical output signal representing a reaction force generated by said impactor striking said fruit;

conveying means for advancing said fruit relatively to said impactors and for rotating said fruit as it is advanced, said impactors being mounted in succession along said conveying means so as to strike said fruit and produce said output signals for a plurality of positions about said fruit;

driving means for applying a driving force to each said impactor to urge said impactor towards said fruit, said driving means being operable so as to terminate application of said driving force to said impactor before said impactor strikes said fruit, whereby said impactor strikes said fruit with an impact in the form of a tap and the respective transducer produces an output signal in the form of a pulse, said output signal being linearly related to said reaction force to which said transducer is subjected by reason of said impact; and means for processing each said output signal to produce a signal indicative of the ripeness of said fruit.

\* \* \* \* \*